US011602493B2

(12) United States Patent
Patel et al.

(10) Patent No.: US 11,602,493 B2
(45) Date of Patent: Mar. 14, 2023

(54) GEL FORMULATIONS

(71) Applicant: BEIERSDORF AG, Hamburg (DE)

(72) Inventors: Jayesh A. Patel, Chandler, AZ (US); Stephen Baldwin, Germantown, TN (US); Tom Meyer, Germantown, TN (US); Anna Erixon, Lander, WY (US); Richard A. Presti, Kinnelon, NJ (US)

(73) Assignee: BEIERSDORF AG, Hamburg (DE)

( * ) Notice: Subject to any disclaimer, the term of this patent is extended or adjusted under 35 U.S.C. 154(b) by 0 days.

(21) Appl. No.: 16/612,114

(22) PCT Filed: May 11, 2018

(86) PCT No.: PCT/US2018/032184
§ 371 (c)(1),
(2) Date: Nov. 8, 2019

(87) PCT Pub. No.: WO2018/209163
PCT Pub. Date: Nov. 15, 2018

(65) Prior Publication Data
US 2020/0281822 A1    Sep. 10, 2020

Related U.S. Application Data

(60) Provisional application No. 62/504,910, filed on May 11, 2017.

(51) Int. Cl.
| A61K 8/04 | (2006.01) |
| A61K 8/27 | (2006.01) |
| A61K 8/34 | (2006.01) |
| A61K 8/37 | (2006.01) |
| A61K 8/81 | (2006.01) |
| A61K 8/895 | (2006.01) |
| A61K 8/92 | (2006.01) |
| A61Q 17/04 | (2006.01) |

(52) U.S. Cl.
CPC .............. *A61K 8/042* (2013.01); *A61K 8/27* (2013.01); *A61K 8/34* (2013.01); *A61K 8/37* (2013.01); *A61K 8/8182* (2013.01); *A61K 8/895* (2013.01); *A61K 8/927* (2013.01); *A61Q 17/04* (2013.01); *A61K 2800/10* (2013.01); *A61K 2800/244* (2013.01); *A61K 2800/31* (2013.01)

(58) Field of Classification Search
None
See application file for complete search history.

(56) References Cited

U.S. PATENT DOCUMENTS

| 3,710,538 | A | 1/1973 | Lowy et al. |
| 3,970,584 | A | 7/1976 | Hart et al. |
| 4,670,272 | A | 6/1987 | Chen et al. |
| 4,777,041 | A | 10/1988 | Mercado |
| 5,560,859 | A | 10/1996 | Hailmann et al. |
| 5,858,343 | A | 1/1999 | Szymczak |
| 6,322,776 | B1 | 11/2001 | Ortega et al. |
| 2004/0052826 | A1 | 3/2004 | Fernandez-Kleinlein et al. |
| 2004/0170586 | A1* | 9/2004 | Ferrari ............... A61K 8/894 424/63 |
| 2004/0197270 | A1 | 10/2004 | Mundschenk |
| 2004/0241099 | A1 | 12/2004 | Popp et al. |
| 2004/0247534 | A1 | 12/2004 | Stoltz |
| 2004/0258627 | A1 | 12/2004 | Riedel et al. |
| 2004/0258628 | A1 | 12/2004 | Riedel et al. |
| 2005/0053632 | A1* | 3/2005 | Schafer ............... A61K 8/41 424/401 |
| 2005/0079142 | A1 | 4/2005 | Brunckhorst et al. |
| 2008/0138296 | A1 | 6/2008 | Tamarkin et al. |
| 2008/0253973 | A1 | 10/2008 | Tamarkin et al. |
| 2008/0260655 | A1 | 10/2008 | Tamarkin et al. |
| 2010/0266649 | A1* | 10/2010 | Maitra ............... A61K 8/19 424/401 |
| 2011/0281827 | A1 | 11/2011 | Tamarkin et al. |
| 2012/0065163 | A1* | 3/2012 | Zhao ............... A61Q 19/008 514/63 |
| 2012/0087872 | A1 | 4/2012 | Tamarkin et al. |

(Continued)

FOREIGN PATENT DOCUMENTS

| AU | 2017263531 A2 | 10/2018 |
| AU | 2017263533 A2 | 10/2018 |

(Continued)

OTHER PUBLICATIONS

Coppertone Sport SPF 15, https://dailymed.nlm.nih.gov/dailymed/lookup.cfm?setid=27f80779-1b01-7522-e054-00144ff8d46c, hereafter Coppertone), accessed Jan. 15, 2021. (Year: 2015).*
International Application No. PCT/US2018/032184, International Search Report dated Jul. 25, 2018, 5 pages.
Mintel, "Dry Touch Oil Free Sunscreen Spray SPF 50" Online, 2016, XP002783084.
Mintel, "High Performance Sunscreen SPF 50", Online, 2016, XP002783085.
International Search Report and Written Opinion received in PCT/US2017/032292 dated Jul. 26, 2017, pp. 10.
International Preliminary Report received in PCT/US2017/032292 dated Nov. 13, 2018, pp. 7.

(Continued)

Primary Examiner — Melissa L Fisher
(74) Attorney, Agent, or Firm — Liang & Hennessey LLP; Stanley D. Liang

(57) ABSTRACT

An anhydrous alcohol gel formulation. The gel formulation comprises one or more film forming agents, one of which is TM-Si 5. The gel formulation comprises active agent(s), which differs based on the purpose of the gel formulation. In certain embodiments, the gel formulation comprises one or more emollients. In certain embodiments, the gel formulation comprises one or more viscosity increasing agents. In certain embodiments, the gel formulation comprises Zinc Oxide. The formulation optionally comprises other ingredients. Such optional ingredients include: a skin conditioning and/or bulking agent; a fragrance, such as, for example and without limitation, Fragrance SZ-2108 MOD 2010; etc.

7 Claims, No Drawings

(56) References Cited

U.S. PATENT DOCUMENTS

| | | |
|---|---|---|
| 2012/0213712 A1 | 8/2012 | Kasai et al. |
| 2012/0288462 A1 | 11/2012 | Lebok et al. |
| 2012/0288465 A1 | 11/2012 | Loechel |
| 2013/0011341 A1 | 1/2013 | Nguyen et al. |
| 2013/0233310 A1 | 9/2013 | Hilgers et al. |
| 2014/0079648 A1 | 3/2014 | Cohen |
| 2014/0120039 A1 | 5/2014 | Baldwin et al. |
| 2014/0131395 A1 | 5/2014 | Chang |
| 2016/0101051 A1 | 4/2016 | Tamarkin et al. |
| 2019/0142709 A1 | 5/2019 | Baldwin et al. |
| 2019/0151207 A1 | 5/2019 | Baldwin et al. |
| 2019/0282463 A1 | 9/2019 | Baldwin et al. |
| 2019/0282464 A1 | 9/2019 | Baldwin et al. |
| 2019/0367256 A1 | 12/2019 | Baldwin et al. |

FOREIGN PATENT DOCUMENTS

| | | |
|---|---|---|
| CN | 1217650 A | 5/1999 |
| CN | 1713891 A | 12/2005 |
| CN | 103547247 A | 1/2014 |
| DE | 10229812 A1 | 1/2004 |
| DE | 10304721 A1 | 8/2004 |
| EP | 1391192 A1 | 2/2004 |
| EP | 1508326 A1 | 2/2005 |
| EP | 2319586 A1 | 5/2011 |
| EP | 2636401 A1 | 9/2013 |
| EP | 3454662 A1 | 3/2019 |
| EP | 3454826 A1 | 3/2019 |
| EP | 3454946 A1 | 3/2019 |
| EP | 3454949 A1 | 3/2019 |
| WO | 0103663 A1 | 1/2001 |
| WO | 2004022019 A1 | 3/2004 |
| WO | 2005007516 A2 | 1/2005 |
| WO | 2012154918 A2 | 11/2012 |
| WO | 2017112727 A1 | 6/2017 |
| WO | 2017197193 A1 | 11/2017 |
| WO | 2017197194 A1 | 11/2017 |
| WO | 2017197195 A1 | 11/2017 |
| WO | 2017197196 A1 | 11/2017 |
| WO | 2017197202 A1 | 11/2017 |

OTHER PUBLICATIONS

Aurena Laboratories "SunScreen Bag on Valve", Retrieved from the Internet, Nov. 19, 2014, pgs.
International Search Report and Written Opinion received in PCT/US2017/032277 dated Aug. 1, 2017, pp. 15.
International Preliminary Report received in PCT/US2017/032277 dated Nov. 13, 2018, pp. 10.
International Search Report and Written Opinion received in PCT/US2017/032278 dated Jul. 26, 2017, pp. 9.
International Preliminary Report received in PCT/US2017/032278 dated Nov. 13, 2018, pp. 6.
Mintel, "Hair Styling Foam", Oct. 2013, XP002772098, Online.
Mintel, "Pack Facial Mask", Mar. 2016, XP002772099, Online.
Mintel, "Body Whip Moisture Cream", Jul. 2008, XP002772100, Online.
Mintel, "Body Whip Cream", Aug. 2009, XP002772101, Online.
International Search Report and Written Opinion received in PCT/US2017/032279 dated Jul. 28, 2017, pp. 11.
International Preliminary Report received in PCT/US2017/032279 dated Nov. 13, 2018, pp. 8.
International Search Report and Written Opinion received in PCT/US2017/032281 dated Aug. 1, 2017, pp. 16.
International Preliminary Report received in PCT/US2017/032281 dated Nov. 13, 2018, pp. 11.
Mexican Patent Office, Mexican Official Action for Mexican App. No. MX/a/2018/013754 (dated Jun. 22, 2021), pp. 1-6.
Dailymed, "Coppertone Defend and Care Oil Free Lotion SPF 30." www.dailymed.nlm.nih.gov. Published online Dec. 17, 2015 (Year: 2015).
Australia IP, Examination report No. 1 for standard patent application for Australian App. No. 2017263538 (dated Feb. 25, 2021).
USPTO, Non-Final Rejection of the US Exam Report for U.S. Appl. No. 16/300,270 (dated Jul. 23, 2020).
USPTO, Non-Final Rejection of the US Exam Report on U.S. Appl. No. 16/300,245 ( dated Feb. 5, 2021).
CIPO, Examination Report and Examination Search Report for Canadian App. No. 3,023,714 (dated Mar. 1, 2021).
EPO, Communication pursuant to Article 94(3) EPC for European App. No. 17726753.1.
Australia IP, Examination report No. 1 for standard patent application for Australian App. No. 2017263531 (dated Feb. 25, 2021).
USPTO, Non-Final Rejection of the US Exam Report on U.S. Appl. No. 16/300,245 (dated Jul. 23, 2020).
USPTO, Final Rejection of the US Exam Report on U.S. Appl. No. 16/300,323 (dated Nov. 18, 2020).
CIPO, Examination Report and Examination Search Report for Canadian App. No. 3,023,669 (dated Jan. 29, 2021).
Australia IP, Examination report No. 1 for standard patent application for Australian App. No. 2017263532 (dated Feb. 25, 2021).
CIPO, Examination Report and Examination Search Report for Canadian App. No. 3,023,680 (dated Feb. 17, 2021).
EPO, Communication pursuant to Article 94(3) EPC for European App. No. 17725450.5 (dated Mar. 19, 2021).
Australia IP, Examination report No. 1 for standard patent application for Australian App. No. 2017263533 (dated Feb. 25, 2021).
USPTO, Non-Final Rejection of the US Exam Report on U.S. Appl. No. 16/300,289 (dated Feb. 5, 2021).
CIPO, Examination Report and Examination Search Report for Canadian App. No. 3,023,703 (dated Feb. 12, 2021).
EPO, Communication pursuant to Article 94(3) EPC for European App. No. 17726162.5 (dated Apr. 2, 2021).
EPO, Communication pursuant to Article 94(3) EPC for European App. No. 17725453.9 (dated Mar. 19, 2021).
USPTO, Non-Final Rejection of the US Exam Report on U.S. Appl. No. 16/300,289 (dated Jul. 27, 2020).
USPTO, Non-Final Rejection of the US Exam Report on U.S. Appl. No. 16/300,342 (dated Jul. 8, 2020).
USPTO, Final Rejection of the US Exam Report on U.S. Appl. No. 16/300,342 (dated Dec. 11, 2020).
USPTO, Non-Final Rejection of the US Exam Report on U.S. Appl. No. 16/300,342 (dated Jun. 24, 2021).
USPTO, Non-Final Rejection of the US Exam Report on U.S. Appl. No. 16/300,270 (dated Feb. 5, 2021).
USPTO, Non-Final Rejection of the US Exam Report on U.S. Appl. No. 16/300,270 (dated Jul. 23, 2020).
Chinese Office Action received in Chinese Application No. 201780028415.1 dated Dec. 6, 2021, pp. 14.
Chinese Office Action received in Chinese Application No. 201780028486.1 dated Nov. 8, 2021, pp. 12.

* cited by examiner

GEL FORMULATIONS

TECHNICAL FIELD

This disclosure relates to the field of gel formulations, including gel formulations for topical application, such as, for example, a sunscreen gel formulation.

BACKGROUND

Consumers leading an active life and skin-smart consumers spending time outdoors look for a sunscreen product that spreads easily, absorbs quickly and leaves no undesirable white or sticky residue behind that would interfere with their activities. While clear sprays can deliver on many of these desired attributes, some consumers prefer a lotion sunscreen that gives them more control over the application process. The gel form provides a hybrid clear product alternative that dispenses like a lotion while providing the lighter sensory attributes more like an alcohol spray. A survey of the marketplace and quantitative testing with consumers shows that an optimized sunscreen gel would fill an unmet need. In addition to the desired aesthetic profile described above, other cosmetic benefits, such as moisturization and appropriateness for acne prone skin, are also important performance properties for a sunscreen formulated for active adults.

SUMMARY

This disclosure provides a gel formulation. The gel formulation is anhydrous; the gel formulation is an alcohol gel formulation. The gel formulation comprises one or more film forming agents, one of which is TM-Si 5. The gel formulation comprises active agent(s), which differs based on the purpose of the gel formulation. For example, a gel sunscreen formulation would comprise sunscreen active agents. In certain embodiments, the gel formulation comprises one or more emollients. In certain embodiments, the formulation comprises one or more viscosity increasing agents. In certain embodiments, the one or more viscosity increasing agents include fumed silica, for example, surface-treated fumed silica. In certain further embodiments, a surface-treated fumed silica is a surface-treated fumed silica with polydimethylsiloxane (such as Aerosil® R202). The formulation optionally comprises other ingredients. Such optional ingredients include: a skin conditioning and/or bulking agent, for example, a silicone elastomer, which may give a powdery feel to the product after the alcohol has evaporated rather than an oily feel; a fragrance, such as, for example and without limitation, Fragrance SZ-2108 MOD 2010 (INCI name: fragrance); etc.

This disclosure provides an anhydrous gel formulation comprising about 25% to about 90% alcohol, one or more film forming agents, one of which is octyldodecyl/glyceryl hydroxy stearate dilinoleate dimethicone copolymer, one or more active agents, one or more viscosity increasing agents, one of which is a fumed silica, one or more skin conditioning agents, and one or more emollients. In certain embodiments, the gel formulation of claim 1, comprising between about 40% to about 62% alcohol. In further embodiments, the alcohol comprises ethanol. In certain embodiments, the gel formulation comprises about 0.5% to about 2% octyldodecyl/glyceryl hydroxy stearate dilinoleate dimethicone copolymer. In certain embodiments, the gel formulation comprises about 2% to about 10% Ethylhexyl Isononanoate. In certain embodiments, the gel formulation comprises about 2% to about 10% Dicaprylyl Ether. In certain embodiments, the gel formulation comprises about 0.5% to about 2% Acrylates/C12-22 Alkylmethacrylate Copolymer. In certain embodiments, the gel formulation comprises about 1% to about 5% polyvinylpyrrolidone (Flexilhix™ polymer). In certain embodiments, the gel formulation comprises about 0.25% to about 1% Silica Dimethicone Silylate. In certain embodiments, the one or more skin conditioning agents include silicone elastomer. In certain further embodiments, the one or more skin conditioning agents comprise about 0.5% to about 2% Dimethicone/Vinyl Dimethicone Crosspolymer. In certain embodiments, the gel formulation further comprises a fragrance. In certain embodiments, the gel formulation comprises about 0.25% to about 1% Beeswax. In certain embodiments, the gel formulation comprises Zinc Oxide. In certain embodiments, the gel formulation comprises fumed silica, which comprises surface treated fumed silica. In further embodiments, the fumed silica comprises Silica Dimethicone Silylate.

In certain embodiments, the gel formulation is a sunscreen gel formulation and comprises sunscreen active agents.

In certain embodiments, the gel formulation is a sunscreen gel formulation characterized by one or more properties selected from high spreadability, antipeeling, desired wetness, desired slipperiness, excellent skinfeel, improved skin elasticity, and improved immediate afterfeel, and improved afterfeel 10 minutes after application.

In certain embodiments, the gel formulation is a sunscreen gel formulation characterized by providing moisture in the skin and improving visual signs of dryness and tactile roughness to the skin of a subject upon application of said formulation.

In certain embodiments, the gel formulation further comprises a cooling agent. In further embodiments, the cooling agent is Questice Liquid or Frescolat-x-cool. In yet further embodiments, the gel formulation comprises about 0.05% to about 1% of Questice Liquid. In other embodiments, the gel formulation comprises about 0.05% to about 1% of Frescolat-x-cool.

In another aspect, this disclosure provides a method of using a disclosed gel formulation, comprising applying said formulation on a subject.

Numerous other aspects are provided in accordance with these and other aspects of the invention. Other features and aspects of the present invention will become more fully apparent from the following detailed description and the appended claims.

DETAILED DESCRIPTION

As used herein, the word "a" or "plurality" before a noun represents one or more of the particular noun. For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

This disclosure provides a gel formulation. The gel formulation is anhydrous; the gel formulation is an alcohol gel formulation (thus comprises alcohol). The gel formulation comprises one or more film forming agents, one of which is TM-Si 5. The gel formulation comprises active agent(s), which differs based on the purpose of the gel formulation. For example, a gel sunscreen formulation would comprise sunscreen active agents. In certain embodiments, the gel formulation comprises one or more emollients. In certain embodiments, the formulation comprises one or more viscosity increasing agents. In certain embodiments, the one or more viscosity increasing agents include fumed silica, for example, surface-treated fumed silica. In certain embodiments, a surface-treated fume silica is a surface-treated fume silica with polydimethylsiloxane (such as Aerosil® R202). A formulation comprising fumed silica has superior sensory heuristics (e.g., better skin feel, appearance, etc.) than one without. The formulation optionally comprises other ingredients. Such optional ingredients include, without limitation: a skin conditioning and/or bulking agent, for example, a silicone elastomer, which may give a powdery feel to the product after the alcohol has evaporated rather than an oily feel; a fragrance, such as, for example and without limitation, Fragrance SZ-2108 MOD 2010 (INCI name: fragrance); etc.

In certain embodiments, the gel formulation comprises the emollient Dragoxat 89 (INCI name: Ethylhexyl Isononanoate), which provides the final product a dry feel. Its ester is made from the reaction of isononanoic acid and 2-ethylhexanol and is a low viscous dry emollient, it is a colorless clear liquid, neutral odor with high purity. In certain embodiments, the gel formulation comprises about 1% to about 10% of Dragoxat 89 (INCI name: Ethylhexyl Isononanoate); in further embodiments, the gel formulation comprises about 2% to about 10% of Dragoxat 89; and in further embodiments, the gel formulation comprises about 5% of Dragoxat 89 (INCI name: Ethylhexyl Isononanoate).

In certain embodiments, the gel formulation comprises the emollient Dicaprylyl Ether (INCI name: Dicaprylyl Ether). Dicaprylyl Ether is an ether of coconut oil (or other plant based oil) derived caprylic acid. In certain embodiments, the gel formulation comprises about 1% to about 10% of Dicaprylyl Ether; in further embodiments, the gel formulation comprises about 2% to about 10% of Dicaprylyl Ether; and in further embodiments, the gel formulation comprises about 5% of Dicaprylyl Ether.

In certain embodiments, the gel formulation comprises a silicone elastomer. An example of a silicone elastomer is Dow Corning 9701 Cosmetic Powder (INCI Name: Dimethicone/Vinyl Dimethicone Crosspolymer). Dow Corning 9701 Cosmetic Powder is a copolymer of dimethylpolysiloxane crosslinked with vinyl dimethylpolysiloxane. Dow Corning 9701 Cosmetic Powder may provide the final product with a silky, powdery feel. In certain embodiments, the gel formulation comprises about 1% to about 5% Dimethicone/Vinyl Dimethicone Crosspolymer; in certain embodiments, the gel formulation comprises about 0.5% to about 2% Dimethicone/Vinyl Dimethicone Crosspolymer; in certain further embodiments, the gel formulation comprises about 2% Dimethicone/Vinyl Dimethicone Crosspolymer.

In certain embodiments, the gel formulation comprises about 25% to about 90% alcohol; in further embodiments, the gel formulation comprises between about 40% to about 55% alcohol; in further embodiments, the gel formulation comprises between about 50% to about 51% alcohol; in certain embodiments, the gel formulation comprises between about 60% to about 62% alcohol. Any suitable alcohol may be used. In certain embodiments, an alcohol that is suitable for skincare is used. In certain embodiments, the alcohol comprises a short-chain alcohol. In certain embodiments, the alcohol is ethanol, methanol, isopropanol and blends thereof. In certain embodiments, the alcohol is denatured. In some embodiments, the alcohol is denatured ethanol (SD alcohol 40-B).

In certain embodiments, the gel formulation comprises TM-Si 5. TM-Si 5 (chemical name: octyldodecyl/glyceryl hydroxy stearate dilinoleate dimethicone copolymer, INCI Name: Polyester-27, by SurfaTech Corporation, Lawrenceville Ga. USA) is a film forming polymer; it is a water proofing/water resistant agent. In certain embodiments, the formulation comprises about 1% to about 5% TM-Si 5; in other embodiments, the formulation comprises about 0.5% to about 2% TM-Si 5. In certain embodiments, the formulation comprises about 1% TM-Si 5. In certain embodiments, the formulation comprises about 3% TM-Si 5.

In certain embodiments, the formulation comprises additional film forming agent(s). In certain embodiments, an additional film forming agent is Allianz™ OPT. In certain embodiments, an additional film forming agent is Allianz™ OPT CSG.

Allianz™ OPT (INCI Name: Acrylates/C12-22 Alkylmethacrylate Copolymer; Ashland) is the tetrapolymer emulsion polymerization product of methacrylic acid, methyl methacrylate, butyl acrylate and cetyl-eicosinyl methacrylate. It is a very hydrophobic, high molecular weight, crosslinked polymer. It effectively thickens the oil phase by creating a large hydrophobic network. In certain embodiments, the gel formulation comprises about 0.1% to about 1% Allianz™ OPT. In certain embodiments, the formulation comprises about 0.5% Allianz™ OPT.

In certain embodiments, the gel formulation comprises about 0.5% to about 2% Allianz™ OPT C5G. In further embodiments, the gel formulation comprises about 1% Allianz™ OPT C5G.

In certain embodiments, an additional film forming agent (gellant) is a thickening agent for thickening alcohol-based solutions.

In certain embodiments, a film forming agent is Flexilhix™ polymer. Flexilhix™ polymer (INCI name: polyvinylpyrrolidone [PVP]; Ashland, Columbus Ohio USA) is a thickener/gellant that works under extreme conditions. Capable of providing stability across a wide pH range, this polymer is highly tolerant of salt, provides a pleasant after-feel and requires no neutralization. In certain embodiments, the formulation comprises about 1% to about 5% Flexilhix™ polymer. In further embodiments, the formulation comprises about 2% to about 4% Flexilhix™ polymer. In certain embodiments, the formulation comprises about 3% Flexilhix™ polymer. In certain embodiments, the formulation comprises about 3.5% Flexilhix™ polymer.

In certain embodiments, the gel formulation comprises the film forming agent Wax White NF Pellets (INCI name: Beeswax). In certain embodiments, the gel formulation comprises about 0.1% to about 1% Beeswax; in certain embodiments, the gel formulation comprises about 0.25% to about 1% Beeswax; in certain further embodiments, the gel formulation comprises about 0.5% Beeswax.

In certain embodiments, the formulation comprises about 0.1% to about 1% fumed silica, such as fumed silica surface-treated with polydimethylsiloxane (such as Aerosil® R202). In certain embodiments, the formulation comprises about 0.25% to about 1% fumed silica, such as surface-treated with polydimethylsiloxane (such as Aerosil® R202). In certain embodiments, the formulation comprises about 0.7% fumed silica, such as surface-treated with polydimethylsiloxane (such as Aerosil® R202).

Aerosil® R202 (INCI name: Silica Dimethicone Silylate) is a fumed silica surface-treated with polydimethylsiloxane (a viscosity increasing agent). Its chemical name is silicones and siloxanes, dimethyl, reaction products with silica. It may provide the final product a no shine, matt finish.

In certain embodiments, the gel formulation comprises: alcohol; one or more film forming agents, one of which is octyldodecyl/glyceryl hydroxy stearate dilinoleate dimethicone copolymer; active agent(s), such as sunscreen active agents to make a sunscreen gel formulation; a viscosity increasing agent, such as a fumed silica; additional film forming agents, such as Acrylates/C12-22 Alkylmethacrylate Copolymer, Beeswax, and/or polyvinylpyrrolidone, and a skin conditional agent, such as a silicone elastomer, for example, Dimethicone/Vinyl Dimethicone Crosspolymer; emollient(s), such as Ethylhexyl Isononanoate and Dicaprylyl Ether; (optionally) fragrance and/or other optional ingredients. In certain further embodiments, the gel formulation comprises Zinc Oxide. The percentages of these ingredients may be those listed herein.

As stated, in certain embodiments, the disclosed gel formulation comprises one or more emollients. An emollient helps to smooth and soften the skin, and may also reduce its roughness, cracking or irritation. Non-limiting examples of suitable emollients include, for example and without limitation, mineral oil having a viscosity in the range of 50 to 500 centipoise (cps), lanolin oil, coconut oil, cocoa butter, olive oil, almond oil, macadamia nut oil, aloe extracts such as aloe Vera lipoquinone, synthetic jojoba oils, natural Sonora jojoba oils, safflower oil, corn oil, liquid lanolin, cottonseed oil and peanut oil. In certain embodiments, the emollient is a cocoglyceride, which is a mixture of mono, di and triglycerides of cocoa oil, or Dicaprylyl Ether. Another suitable emollient is, for example, DC 200 Fluid 350, a silicone fluid.

Other suitable emollients may include, for example and without limitation, squalane, castor oil, polybutene, sweet almond oil, avocado oil, calophyllum oil, ricin oil, vitamin D, vitamin E acetate, olive oil, silicone oils such as dimethylopolysiloxane and cyclomethicone, linotenic alcohol, oleyl alcohol, the oil of cereal germs such as the oil of wheat germ, isopropyl palmitate, cotyle palmitate, isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and poly-alcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and aloe Vera extract.

Other suitable emollients that are solids or semi solids at ambient temperatures may be used. Such solid or semi-solid cosmetic emollients include, for example and without limitation, glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more of these emollients can be optionally included in the formulation.

The disclosed gel formulation product can be used for any application that would benefit from such product, including, for example and without limitation, skincare, sunscreen, After Sun care, vitamins, woundcare, etc. For each application, the formulation needs to comprise the corresponding active agent(s) and may further comprise other appropriate ingredients.

In certain embodiments, the gel formulation product is a skincare product, comprising one or more skincare active agents. In certain embodiments, the gel formulation product is a sunscreen or an After-Sun product. In certain embodiments, the gel formulation product may be for woundcare of animals or humans.

A "skincare active agent" includes all those materials regarded as acceptable for use as active skin-protecting ingredients. A skincare active agent includes, for example and without limitation, skin protectant and/or anti-aging agent. Approval by a regulatory agency may sometimes be required for inclusion of active agents in formulations intended for human contact, including but not limited to, sunscreen active ingredients or skin protectant ingredients such as petrolatum, white petrolatum, mineral oil, and dimethicone, as well as agents used as self-tanners, and the like.

In certain embodiments, in addition to the skin-active ingredients already described, the disclosed gel formulation comprises one or more additional skin-active ingredients, such as a humectant and moisturizing ingredients, an anti-aging agent, a depigmenting agent, an anti-wrinkle agent, or an agent that treats oily skin. Non-limiting examples of the one or more active agents include adenosine, hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, and a coenzyme. In some embodiments, the active ingredient is adenosine.

In certain embodiments, the disclosed gel formulation comprises one or more vitamin(s). For example, the vitamin(s) may include ascorbic acid, vitamin A, vitamin E, and/or vitamin B, glycolic acid, allantoin.

In some embodiments, the humectants and moisturizing ingredients are glycerol and its derivatives, urea and its derivatives, Hydrovance marketed by National Starch, lactic acid, hyaluronic acid, AHA, BHA, xylitol, serine, sodium lactate, ectoin and its derivatives, chitosan and its derivatives, collagen, plankton, beta-glucan, and arginine.

Depigmenting agents may be included in the formulation. Depigmenting agents include, for example and without limitation, vitamin C and its derivatives and especially vitamin CG, CP and 3-O ethyl vitamin C, alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, ceramides and their counterparts.

The term "anti-wrinkle active" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Exemplary anti-wrinkle actives may be chosen from: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof.

Examples of such anti-wrinkle active compounds are: adenosine and its derivatives and retinol and its derivatives, such as retinol palmitate; ascorbic acid and its derivatives, such as magnesium ascorbyl phosphate and ascorbyl glucoside; tocopherol and derivatives thereof, such as tocopheryl acetate; nicotinic acid and its precursors, such as nicotinamide; ubiquinone; glutathione and precursors thereof, such as L-2-oxothiazolidine-4-carboxylic acid, the compounds C-glycosides and their derivatives, as for example, described, e.g., in EP-1345919, and C-beta-D-xylopyranoside-2-hydroxypropane as described in, e.g., EP-1345919; plant extracts, including sea fennel and extracts of olive leaves, as well as plant and hydrolysates thereof, such as rice protein hydrolysates or soybean proteins.

In some embodiments, the disclosed gel formulation comprises a skin-active ingredient that addresses oily skin. These actives can be sebo-regulating or antiseborrhoeic agents capable of regulating the activity of sebaceous glands. These include, for example and without limitation: retinoic acid, benzoyl peroxide, sulfur, vitamin B6.

The disclosed gel formulation may comprise one or more peptides. Herein, "peptide" refers to peptides containing ten or fewer amino acids, their derivatives, isomers, and complexes with other species such as metal ions (for example, copper, zinc, manganese, and magnesium). As used herein, peptide refers to both naturally occurring and synthesized peptides. In certain embodiments, the peptides are di-, tri-, tetra-, penta-, and hexa-peptides, their salts, isomers, derivatives, and mixtures thereof. Examples of useful peptide derivatives include, but are not limited to, peptides derived from soy proteins, carnosine (beta-alanine-histidine), palmitoyl-lysine-threonine (pal-KT) and palmitoyl-lysine-threonine-threonine-lysine-serine.

Any suitable sunscreen active agents may be part of the disclosed sunscreen gel formulation. Approved sunscreen active agents in the United States and elsewhere include, without limitation, paraaminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, octisalate, sulisobenzone, trolamine salicylate, titanium dioxide and zinc oxide, and the like. Several other sunscreen active ingredients are accepted for use in other countries. Some non-limiting examples from outside the U.S. include Tinosorb M, Tinosorb S, Uvinul T-150, UVA sorb HEB, Uvinul A Plus, Neo Heliopan AP, Neo Heliopan MBC, and the like.

It is typical to use combinations of two or more skincare active agents in a formulation. The amount of skincare active agent or agents may be present in an amount that is consistent with the guidelines of the FDA or other regulatory bodies. The use of a combination of active agents is especially true for sunscreen formulations to achieve higher levels of ultraviolet absorption or to provide useful absorption over a wider range of ultraviolet wavelengths than can be the case with a single active component. Preferably, the sunscreen active agent or agents is present in an amount that is consistent with the FDA sunscreen monograph for sunscreen active agent or agents that are believed to provide the requisite SPF in accordance with the FDA monograph for such sunscreens. Other skin care active agents include sunless tanning active agents, skin protectant active agent emollients, insect repelling agents, and the like. And other agents known in the art.

After Sun product is specially formulated to cool, soothe, calm, and re-hydrate (moisturize) a sunburned or stressed skin, and to lessen the pain or itch of a sunburned body. The active agents in After Sun products are known in the art and any of which is within the scope of this invention. After Sun Actives are ingredients that can provide the following (but not limited) effects on skin: cooling; soothing; calming; re-hydrating (moisturizing); or relief pain/itch associated with sunburn. As an example, and without limitation, an After Sun formulation contains Glycerin, Panthenol, and Aloe Barbadensis Leaf Juice to provide cool and moisturizing effects on skin. As another example, and without limitation, another After Sun formulation contains Lidocaine as an active to provide sunburn pain/itch relief.

Other active agents are contemplated. These include, for example and without limitation, sunscreen active agents, After Sun active agents, vitamins, food, etc. Any active agents that can be included as a gel formulation are within the scope of this invention.

Any suitable active agents are within the scope of the disclosed invention.

In certain embodiments, the formulation is a sunscreen gel and the one or more active agents include one or more sunscreen active agents.

In certain embodiments, the disclosed formulation comprises a cooling agent. Examples of cooling agent includes without limitation, Questice Liquid and Frescolat-x-cool. In certain embodiments, the gel formulation comprises about 0.05% to about 1% of Questice Liquid. In certain embodiments, the gel formulation comprises about 0.05% to about 1% of Frescolat-x-cool. Questice Liquid is an ester of L-menthol and L-pyrrolidone carboxylic acid (PCA), linked by a relatively weak bond. Frescolat-x-cool is also referred to as Menthyl Ethylamido Oxalate.

In certain embodiments, the gel formulation comprises Zinc Oxide. In certain embodiments, the gel formulation comprises about 5% to 40% Zinc Oxide. In certain embodiments, the gel formulation comprises about 15% to 25% Zinc Oxide. In certain embodiments, the gel formulation comprises about 20% Zinc Oxide. The Zinc Oxide may be Zinc Oxide nanoparticles, such as Zinc Nano 20. In certain embodiments, the gel formulation comprises Zinc Oxide.

In certain embodiments, the physical stability of the gel products obtained may also be characterized by means of these tests: determination of the organoleptic characteristics (e.g., aspect, color, odor), characterization of the texture (e.g., thickness, greasy, non-greasy), and characterization of the spreadability.

Insect repelling components are also a desirable ingredient in certain skincare and sunscreen formulations, if the formulations are to be used by persons engaged in outdoor activities. The most widely used insect repelling agent for personal care products is N,N-Diethyl-m-toluamide, frequently called "DEET" and available in the form of a concentrate containing at least about 95 percent DEET. Other synthetic chemical repellents include, for example and without limitation, dimethyl phthalate, ethyl hexanediol, indalone, di-n-propylisocinchoronate, bicycloheptene, dicarboximide, IR3535 (3-[N-Butyl-N acetyl]-aminopropionic acid, ethyl ester; available from Merck KGaA)) and tetrahydrofuraldehyde. Certain plant-derived materials also have insect repellent activity, including citronella oil and other sources of citronella (including lemon grass oil), limonene, rosemary oil and eucalyptus oil. Choice of an insect repellent for incorporation into the skincare or sunscreen emulsion will frequently be influenced by the odor of the repellent. The amount of repellent agent used will depend upon the choice of agent; DEET is useful at high concentrations, such as up to about 15 percent or more, while some of the plant-derived substances are typically used in much lower amounts, such as 0.1 percent or less.

The disclosed formulation/formulations may contain a wide range of additional, optional components. For example, the CTFA Cosmetic Ingredient Handbook, Seventh Edition, 1997, the Eighth Edition, 2000, and the personal care council website (http://www.personalcarecouncil.org/) describe a wide variety of cosmetic and pharmaceutical ingredients commonly used in skin care formulations, which are suitable for use in the formulations of the present invention. Examples of these functional classes disclosed in these references include, for example and without limitation, absorbents, abrasives, anticaking agents, antioxidants, binders, biological additives, buffering agents, bulking agents, chelating agents, chemical additives, colorants, cosmetic astringents, cosmetic biocides, cryoprotectants, film stabilizers, denaturants, drug astringents, external analgesics, film formers, fragrance components, humectants, pacifying agents, pH adjusters, plasticizers, preservatives, propellants, reducing agents, skin bleaching agents, skin-conditioning agents (emollients, humectants, miscellaneous, and occlusive), skin protectants, solvents, SPF enhancers/boosters, hydrotropes, sunscreen agents, ultraviolet light absorbers, and viscosity increasing agents.

The gel formulations may further comprise skin protectant active agents. Suitable examples include, for example and without limitation, (with preferred weight percent ranges), Allantoin (0.5 to 2 percent); Aluminum hydroxide gel (0.15 to 5 percent), Calamine (1 to 25 percent); Cocoa butter (greater than 50 percent); Cod liver oil (5 to 14 percent); Dimethicone (1 to 30 percent); Glycerin (20 to 45 percent); Hard fat (greater than 50 percent); Kaolin (4 to 20 percent); Lanolin (12.5 to 50 percent); Mineral oil (greater than 50 percent); Petrolatum (greater than 30 percent); Topical starch (10 to 98 percent); White petrolatum (greater than 30 percent); Zinc acetate (0.1 to 2 percent); Zinc carbonate (0.2 to 2 percent); and Zinc oxide (1 to 25 percent). Additional skin protectant active agents may include Colloidal oatmeal or Sodium bicarbonate.

An antioxidant may be part of the disclosed formulation. An antioxidant is a natural or synthetic substance added to the sunscreen to protect from or delay its deterioration due to the action of oxygen in the air (oxidation) and to protect the skin from sun damage. Antioxidants prevent oxidative deterioration which may lead to the generation of rancidity and nonenzymatic browning reaction products. Typical suitable antioxidants include, for example and without limitation, propyl, octyl and dodecyl esters of gallic acid, butylated hydroxyanisole (BHA, usually purchased as a mixture of ortho and meta isomers), butylated hydroxytoluene (BHT), nordihydroguaiaretic acid, Oxynex (Oxynex ST liquid is a mixture of diethylhexyl syringylidenemalonate and caprylic/capric triglyceride), Vitamin A, Vitamin E and Vitamin C. One or more antioxidants can optionally be included in the formulation in an amount ranging from about 0.001 to about 5 weight percent, preferably about 0.01 to about 0.5 percent.

Chelating agents may be part of the disclosed formulation. Chelating agents are substances used to chelate or bind metallic ions, such as with a heterocyclic ring structure so that the ion is held by chemical bonds from each of the participating rings. Suitable chelating agents include, for example and without limitation, citric acid, ethylene diaminetetraacetic acid (EDTA), EDTA disodium, calcium disodium edetate, EDTA trisodium, citric acid, EDTA tetrasodium and EDTA dipotassium. One or more chelating agents can optionally be included in the formulation in amounts ranging from about 0.001 to about 0.2 weight percent preferably about 0.01% weight percent.

Fragrances are aromatic substances which can impart an aesthetically pleasing aroma to the skincare or sunscreen formulation and may be part of the disclosed formulation. Typical fragrances include, for example and without limitation, aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. Both types are considered to be within the scope of the present invention.

In some embodiments, an SPF enhancer or booster, including styrene/acrylates copolymer (such as Sunspheres PGL, commercially available from Dow Chemical), and/or skin active agents, and/or anti-oxidants, may be optionally added to the formulation.

The disclosed formulation may be used as an After Sun formulation. As used herein, an After Sun formulation is defined as a formulation that can be administered after a user has been in the sun for any amount of time and is a formulation that provides a soothing or healing effect that is pleasant to the user. Such a formulation can contain, for instance, aloe Vera, vitamins A and E, cooling agents, moisturizers, redness-reducing agents and the like.

The present formulation may be used as self-tanning formulation or for sunless tanning. As used herein, the term "sunless-tanning" or "self-tanning formulations" refer to formulations which, when applied to human skin, impart thereto an appearance similar to that achieved by exposing the skin to natural or artificial sunlight. Examples of sunless tanning active agents are described in U.S. Pat. Nos. 6,482,397, 6,261,541, and 6,231,837. Such sunless tanning compositions typically comprise, in addition to an artificial tanning effective amount of a self-tanning agent, effective amounts of a formulation coloring agent and a cosmetically acceptable carrier adapted for topical application to human skin. The self-tanning agents can also include those formulations generally accepted in the art for application to human skin, and which, when so applied, react therein with amino acids so as to form pigmented products. Such reactions give the skin a brown appearance, similar to the color obtained upon exposing it to sunlight for periods of time sufficient to tan the skin. Suitable self-tanning agents include, without limitation, alpha-hydroxy aldehydes and ketones, glyceraldehyde and related alcohol aldehydes, various indoles, imidazoles and derivatives thereof, and various approved pigmentation agents. Presently preferred herein as self-tanning agents are the alphahydroxy aldehydes and ketones. Most preferably, the self-tanning agent is dihydroxyacetone ("DHA"). Other suitable self-tanning agents include, without limitation, methyl glyoxal, glycerol aldehyde, erythrulose, alloxan, 2,3-dihydroxysuccindialdehyde, 2,3-dimethoxysuccindialdehyde, 2-amino-3-hydroxysuccindialdehyde and 2-benzylamino-3-hydroxysuccindialdehyde.

Certain embodiments provide a high SPF alcohol gel that does not feel slimy to the user or peels off easily. It is a waterless, anhydrous alcohol gel. Some descriptive words associated with the product include dry, non-greasy, anti-peeling.

Some of the characteristics of the disclosed gel formulation, such as a sunscreen gel, are: antipeeling; dry and non-greasy (sweating, long-lasting), Non-Slimy; Durability—Water/Wear resistance; good sensory feel; Silky/powdery feel; and spreadability.

In certain embodiments, a disclosed gel formulation, such as a disclosed sunscreen gel formulation, is characterized by providing moisture in the skin and improving visual signs of dryness and tactile roughness to the skin of a subject upon application of said formulation. In certain embodiments, the improvement visual signs of dryness and tactile roughness to the skin of a subject lasts for at least 8 hours after application.

In certain embodiments, the disclosed gel formulation is characterized by one or more properties selected from high spreadability, antipeeling, desired wetness, desired slipperiness, excellent skinfeel, improved skin elasticity, and improved immediate afterfeel, and improved afterfeel 10 minutes after application.

In certain embodiments, the disclosed gel formulation is characterized by providing moisture in the skin and improving visual signs of dryness and tactile roughness to the skin of a subject upon application of the formulation.

This disclosure also provides a method of making a gel formulation disclosed herein. The method comprising:
(1) adding a short-chain alcohol, such as alcohol SD40-B (denatured ethanol), to a first container and mixing with a Tri-Blade propeller;
(2) slowly mixing in a film forming agent, e.g., polyvinylpyrrolidone, keeping covered;
(3) adding active agent(s), such as sunscreen active agent(s) to make a sunscreen gel formulation, followed by, adding octyldodecyl/glyceryl hydroxy stearate dilinoleate dimethicone copolymer (a film forming agent), a viscosity increasing agent, such as fumed silica, such as Silica Dimethicone Silylate, additional film forming agents, such as Acrylates/C12-22 Alkylmethacrylate Copolymer, and a skin conditioning agent, such as a silicone elastomer, for example, Dimethicone/Vinyl Dimethicone Crosspolymer, until in solution;
(4) heating emollient(s), such as Ethylhexyl Isononanoate and Dicaprylyl Ether, and optionally one or more additional film forming agents, such as Beeswax, to 70-75° C. in a second container until melted and then adding the solution in the second container to the solution of the first container;
(5) (optionally) adding fragrance and/or other ingredients; and
(6) adding more alcohol, such as SD40-B, to reach desired volume.
The percentages of these ingredients may be those listed herein.

This disclosure also provides a method of using a gel formulation disclosed herein, comprising applying the formulation on a subject, who may be in need thereof. The subject may be a human subject. The subject may be an active human being or a skin-smart human being who spend time outdoors and needs to apply a sunscreen product. The subject may be a person who is working outdoors or at the beach and is thus in need of having sunscreen applied on this person's skin. The subject may be an animal, such as a domestic pet or livestock.

Although specific suppliers of commercially available ingredients may be listed herein, it is understood that these products may be available from additional suppliers and that the instant invention is not limited to only that ingredient from the specifically cited supplier. Rather the supplier is being provided as an example of what is commercially available.

EXAMPLES

For this invention to be better understood, the following examples are set forth. These examples are for purposes of illustration only and are not be construed as limiting the scope of the invention in any manner.

Example 1. Exemplary Gel Formulations

TABLE 1

| An Exemplary Sunscreen Gel Formulation of the disclosure | |
|---|---|
| Alcohol SD 40-B | 55.70% |
| polyvinylpyrrolidone | 3.00% |
| Avobenzone, USP | 3.00% |
| Octisalate, USP | 4.50% |
| Octocrylene, USP | 9.00% |
| Homosalate, USP | 10.00% |
| Polyester-27 | 1.00% |
| Silica Dimethicone Silylate | 0.70% |
| Acrylates/C12-22 Alkylmethacrylate Copolymer | 0.50% |
| Dimethicone/Vinyl Dimethicone Crosspolymer | 2.00% |
| Ethylhexyl Isononanoate | 5.00% |
| Beeswax | 0.50% |
| Dicaprylyl Ether | 5.00% |
| Fragrance | 0.10% |
| TOTALS: | 100.00% |

TABLE 2

| An Exemplary SPF 30 Sunscreen Gel of This Disclosure | |
|---|---|
| INCI Name | Quantity (g) per 100 gram formula |
| SD Alcohol 40-B | 55.70 |
| Homosalate | 10.00 |
| Octocrylene | 9.00 |
| Dicaprylyl Ether | 5.00 |
| Ethylhexyl Isononanoate | 5.00 |
| Ethylhexyl Salicylate | 4.50 |
| Butyl Methoxydibenzoylmethane | 3.00 |
| Polyvinylpyrrolidone | 3.00 |
| Dimethicone/Vinyl Dimethicone Crosspolymer | 1.94 |
| Polyester-27 | 1.00 |
| Silica Dimethicone Silylate | 0.70 |
| Beeswax | 0.50 |
| Acrylates/C12-22 Alkyl Methacrylate Copolymer | 0.50 |
| Fragrance | 0.10 |
| Silica | 0.06 |
| Total | 100.00 |

TABLE 3

| An Exemplary SPF 50 Sunscreen Gel of This Disclosure | |
|---|---|
| INCI Name | Quantity (g) per 100 gram formula |
| SD Alcohol 40-B | 50.70 |
| Homosalate | 10.00 |
| Octocrylene | 9.00 |
| Dicaprylyl Ether | 5.00 |
| Ethylhexyl Isononanoate | 5.00 |

TABLE 3-continued

An Exemplary SPF 50 Sunscreen Gel of This Disclosure

| INCI Name | Quantity (g) per 100 gram formula |
|---|---|
| Benzophenone-3 | 5.00 |
| Ethylhexyl Salicylate | 4.50 |
| Butyl Methoxydibenzoylmethane | 3.00 |
| Polyvinylpyrrolidone (PVP) | 3.00 |
| Dimethicone/Vinyl Dimethicone Crosspolymer | 1.94 |
| Polyester-27 | 1.00 |
| Silica Dimethicone Silylate | 0.70 |
| Beeswax | 0.50 |
| Acrylates/C12-22 Alkyl Methacrylate Copolymer | 0.50 |
| Fragrance | 0.10 |
| Silica | 0.06 |
| Total | 100.00 |

Example 2

Aesthetic Properties of Disclosed Sunscreen Gel

Because the sensory properties are important drivers of liking, and consequently motivators for better compliance among consumers using sunscreens, a study is done to objectively define and measure the intensity of certain aesthetic skin feel properties of the gel product. Qualitative sensory assessments were initially conducted with consumers to establish benchmarks that reflected preferences and target attributes specifically desired by Active Adult sunscreen users.

Those physical benchmarks were included along with prototype formulations in an iterative sequence of quantitative Descriptive Analysis Studies to create spider maps indicating alignment of the gel product with the target sensory profile. This research confirmed that the skin feel attributes of the gel sunscreen were appropriately optimized for consumer acceptance.

The standard study design involves monadic assessments of sunscreen formulations in a randomized and balanced complete block design and estimate mean values for each sensory attribute for each product. A trained panel performs all assessments using the Spectrum Descriptive Analysis Method. The trained panelists (11) are from Sensory Spectrum, 222 Oak Avenue Kannapolis, N.C. 28081.

The analyses provide both descriptive (qualitative) and intensity measures (quantitative) of the products. The descriptive analysis methodologies are based on those described in ASTM Manual 26, Sensory Testing Methods, 2nd Ed, E. Chambers IV, editor, and ASTM Manual on Descriptive Analysis Testing for Sensory Evaluation, R. Hootman, editor, and Sensory Evaluation Techniques by Meilgard, Civille and Carr.

The Spectrum Descriptive Analysis Method grounds itself in the use of published and internal intensity reference scales to define intensity boundaries in sensory experiences. Skin-feel Panelists are trained using the Spectrum Descriptive Analysis Method for personal care products. They are selected based on their ability to detect and discriminate differences in visual and tactile properties. Panelists are trained on a universal scale that focuses on intensity or strength of the signal, coupled with detailed description and definitions of sensory attributes and use of calibrated training samples. All panelists receive a minimum of 100 hours of training and practice prior to commissioning of client research and are extensively trained in evaluation of lotions, creams, gels, and related product forms.

Attribute intensity is rated on an intensity scale with 0=none and 100=very strong/very high. The intensity scale uses 1-point increments, allowing for 101 points of differentiation. Panelists are trained to use the scale in a similar way across panelists and across samples. Use of a universal scale allows attributes to be compared in intensity to one another, (e.g. comparing intensity of slippery feel to intensity of sticky feel), as well as for comparison of samples within and across studies and products having shared attributes.

All data are collected from the individual respondents, and evaluations are replicated. Data collection of this type is well suited to correlation with both instrumental and consumer research data.

The tested product contains sunscreen ingredients that comply with the types, combinations and concentrations specified by the 1999 FDA Final Sunscreen Monograph or subsequent FDA regulations. The product was over-labeled and bulk packaged and/or over-labeled in its marketed packaging. The product is a sunscreen gel SPF50, disclosed herein.

Two 4"×2" rectangular evaluation sites were scribed on each volar forearm. Using an automatic pipette, panel leader or technician delivered 0.1 cc of product to the evaluation site. Panelists spread the product within the rectangle with index or middle finger, using a gentle oval motion, at a rate of two strokes per second.

The study sampling plan utilized a randomized design to alternate and balance the evaluation sites. Samples were replicated so that each sample was seen twice by each panelist. After data is collected, means were calculated using Microsoft Excel.

TABLE 4

Rubout Attributes: Gel SPF 50

| Attributes | mean | min | max | range |
|---|---|---|---|---|
| Wetness | 68.8 | 65.0 | 74.0 | 9.0 |
| Spreadability | 63.5 | 60.0 | 70.0 | 10.0 |
| Coolness | 12.7 | 5.0 | 23.0 | 18.0 |
| Thickness | 30.1 | 18.0 | 35.0 | 17.0 |
| Slipperiness | 77.1 | 68.0 | 87.0 | 19.0 |
| Oil | 23.4 | 10.0 | 35.0 | 25.0 |
| Wax | 8.18 | 4.0 | 18.0 | 14.0 |
| Grease | 28.5 | 15.0 | 43.0 | 28.0 |
| Whitening | 0.45 | 0.0 | 5.0 | 5.0 |
| Pilling-Visual | 13.7 | 0.0 | 25.0 | 25.0 |
| Pilling-Tactile | 18.3 | 2.0 | 25.0 | 23.0 |
| Pilling-# of Rubs | 17.6 | 6.0 | 30.0 | 24.0 |
| Rubs to Absorbency | 30.0 | 19.0 | 45.0 | 26.0 |

The disclosed gel SPF50 scored high on spreadability, wetness, and slipperiness, which were identified by consumers as desirable attributes for a sunscreen gel.

TABLE 5

Immediate Afterfeel Was Favorable

| Attributes | mean | min | max | range |
|---|---|---|---|---|
| Gloss | 20.7 | 15.0 | 28.0 | 13.0 |
| Whitening | 0.2 | 0.0 | 5.0 | 5.0 |
| Stickiness | 1.5 | 0.0 | 6.0 | 6.0 |
| Tautness | 16.8 | 15.0 | 32.0 | 17.0 |
| Roughness | 18.9 | 14.0 | 28.0 | 14.0 |
| Slipperiness | 78.0 | 70.0 | 86.0 | 16.0 |

TABLE 5-continued

Immediate Afterfeel Was Favorable

|  | mean | min | max | range |
|---|---|---|---|---|
| Thickness Residue | 10.8 | 6.0 | 15.0 | 9.0 |
| Amount Residue | 16.3 | 7.0 | 35.0 | 28.0 |
| Type of Residue |  |  |  |  |
| Oil | 18.0 | 5.0 | 34.0 | 29.0 |
| Wax | 21.0 | 5.0 | 40.0 | 35.0 |
| Grease | 19.7 | 10.0 | 40.0 | 30.0 |
| Silicone | 3.4 | 0.0 | 10.0 | 10.0 |
| Plastic/Coated | 8.5 | 0.0 | 20.0 | 20.0 |
| Pilling-Visual | 7.2 | 0.0 | 25.0 | 25.0 |
| Pilling-Tactile | 12.5 | 0.0 | 30.0 | 30.0 |

TABLE 6

Immediate Afterfeel - Presence of Particulates Not a Concern Gel SPF 50

| Particulate |  |
|---|---|
| Gritty Visual | 0 |
| Grainy Visual | 0 |
| Chalky Visual | 0 |
| Powdery Visual | 0 |
| Peeling/flaky Visual | 5 |
| Gritty Tactile | 2 |
| Grainy Tactile | 2 |
| Chalky Tactile | 2 |
| Powdery Tactile | 1 |
| Peeling/flaky Tactile | 6 |

Count data Panelists note the presence or absence of particulates in the afterfeel (present=1; absent=0). Sample is perceived as having a residue only when the perception occurs in both reps (N=11).

TABLE 7

10-minute Afterfeel Was Favorable Gel SPF 50

|  | mean | min | max | range |
|---|---|---|---|---|
| Attributes |  |  |  |  |
| Gloss | 14.8 | 10.0 | 25.0 | 15.0 |
| Whitening | 0.0 | 0.0 | 0.0 | 0.0 |
| Stickiness | 0.4 | 0.0 | 4.0 | 4.0 |
| Tautness | 16.5 | 15.0 | 31.0 | 16.0 |
| Roughness | 20.0 | 15.0 | 28.0 | 13.0 |
| Slipperiness | 78.9 | 76.0 | 82.0 | 6.0 |
| Thickness Residue | 7.6 | 4.0 | 12.0 | 8.0 |
| Amount Residue | 10.4 | 6.0 | 20.0 | 14.0 |
| Type of Residue |  |  |  |  |
| Oil | 6.0 | 0.0 | 30.0 | 30.0 |
| Wax | 30.8 | 5.0 | 60.0 | 55.0 |
| Grease | 14.2 | 5.0 | 25.0 | 20.0 |
| Silicone | 5.6 | 0.0 | 15.0 | 15.0 |
| Plastic/Coated | 9.9 | 0.0 | 30.0 | 30.0 |
| Pilling-Visual | 1.2 | 0.0 | 10.0 | 10.0 |
| Pilling-Tactile | 3.1 | 0.0 | 15.0 | 15.0 |

TABLE 8

10-minute Afterfeel - Presence of Particulates Not a Concern

| Particulate | Gel SPF 50 |
|---|---|
| Gritty Visual | 0 |
| Grainy Visual | 0 |
| Chalky Visual | 0 |
| Powdery Visual | 0 |
| Peeling/flaky Visual | 1 |
| Gritty Tactile | 1 |
| Grainy Tactile | 1 |
| Chalky Tactile | 2 |
| Powdery Tactile | 1 |
| Peeling/flaky Visual | 2 |

Count data Panelists note the presence or absence of particulates in the afterfeel (present=1; absent=0). Sample is perceived as having a residue only when the perception occurs in both reps (N=11).

TABLE 9

Product Manipulation and Appearance Were Favorable Gel SPF 50

| Attributes | Mean | min | max | range |
|---|---|---|---|---|
| MANIPULATION |  |  |  |  |
| Firmness | 34.4 | 30.0 | 39.0 | 9.0 |
| Stickiness | 23.6 | 20.0 | 25.0 | 5.0 |
| Cohesiveness | 7.8 | 5.0 | 10.0 | 5.0 |
| Peaking | 14.8 | 10.0 | 23.0 | 13.0 |
| APPEARANCE |  |  |  |  |
| Integrity of Shape-Immediate | 88.8 | 86.0 | 92.0 | 6.0 |
| Integrity of Shape-10 seconds | 88.5 | 85.0 | 92.0 | 7.0 |
| Gloss | 63.5 | 60.0 | 68.0 | 8.0 |

There were no reported adverse events.

Example 3. A Method of Making Disclosed Sunscreen Gels

TABLE 10

SPF50 Gel Sunscreen Formula

Dry Percent W/W

Part A

| 50.7000 | Alcohol SD 40-B |
| 3.0000 | Polyvinyl pyrrolidone |

Part B

| 10.0000 | Homosalate, USP |
| 4.5000 | Octisalate, USP |
| 3.0000 | Avobenzone, USP |
| 5.0000 | Oxybenzone, USP |
| 9.0000 | Octocrylene, USP |
| 1.0000 | Polyester-27 |
| 0.7000 | Silica Dimethicone Silylate |
| 0.5000 | Acrylates/C12-22 Alkylmethacrylate Copolymer |
| 2.0000 | Dimethicone/Vinyl Dimethicone Crosspolymer |

Part C

| 5.0000 | Ethylhexyl Isononanoate |
| 0.5000 | Beeswax |
| 5.0000 | Dicaprylyl Ether |

Part D

| 0.1000 | Fragrance |

Part E

| 0.0000 | Alcohol SD 40-B |

TABLE 11

SPF30 Gel Sunscreen Formula

| Dry Percent W/W | |
|---|---|
| 55.7000 | Alcohol SD 40-B |
| 3.0000 | polyvinylpyrrolidone |
| 10.0000 | Homosalate, USP |
| 4.5000 | Octisalate, USP |
| 3.0000 | Avobenzone, USP |
| 9.0000 | Octocrylene, USP |
| 1.0000 | Polyester-27 |
| 0.7000 | Silica Dimethicone Silylate |
| 0.5000 | Acrylates/C12-22 Alkylmethacrylate Copolymer |
| 2.0000 | Dimethicone/Vinyl Dimethicone Crosspolymer |
| 5.0000 | Ethylhexyl Isononanoate |
| 0.5000 | Beeswax |
| 5.0000 | Dicaprylyl Ether |
| 0.1000 | Fragrance |
| Q. S. | Alcohol SD 40-B |
| Totals 100.0000 | |

TABLE 12

Manufacturing Directions

| Step 1 | Add Alcohol of Part A to a suitable container and mix with a Tri-Blade propeller. Slowly sprinkle polyvinylpyrrolidone while mixing to minimize clumps. Increase mixing speed as necessary. Record start time and stop time. KEEP BATCH WELL COVERED. |
|---|---|
| Step 2 | Add the ingredients of Part B in the listed order to the batch and mix until all the ingredients are in solution. Record start time and stop time. |
| Step 3 | To a suitable container, add the Dragoxat 89 and White Wax of Part C and mix while heating to 70-75° C. until melted. Remove from heat and add Dicaprylyl Ether. Mix and cool to room temperature. Add Part C to the batch of Part AB and mix well. Record start time and stop time. Record Temp. |
| Step 4 | Add the Fragrance SZ-2108 and mix well. Record start time and stop time. |
| Step 5 | Q.S. the batch with Alcohol of Part E and mix well for at least 20 minutes. 1. Record Batch + Tare Wt. (weight when finished); 2. Tare Wt (weight of empty beaker and prop); 3. Batch Wt. (subtract line 2 from line 1) 4. Theoretical Wt. (weight of batch) 5. QS Amount (subtract line 4 from line 3) |

Example 4

Disclosed Gel Sunscreen's Effect on Skin Conditioning

In addition to providing guidance for optimization of the sensory profile for a gel product, consumers also noted a concern that an alcohol based product could dry the skin. A study was conducted on dry skin measuring immediate and sustained (up to 8 hours) hydrating effects of the sunscreen gel. Overall results of this double-blind, single-center, controlled study indicated that 1 application of Sunscreen Gel SPF 50 and 2 applications (at 2 hours apart) of Sunscreen Gel SPF 50, which is consistent with "apply every 2 hours" monograph labeling requirements, showed that both application regimens were effective in providing moisturization in the skin and improving visual signs of dryness and tactile roughness when compared to the untreated control site over the course of 8 hours on women with mild to moderate dry skin and roughness on the lateral lower legs under these study conditions.

The study was conducted to measure the cosmetic effects (primarily moisturization) of application and reapplication of test materials to the skin over a period of 8 hours (480 minutes). A total of 43 subjects completed the study.

A total of 2 test sites were marked on the lateral side of each subject's lower legs (4 sites per subject). A clinician applied disclosed Sunscreen Gel SPF 50 once over the 8-hour study duration or twice over the 8-hour study duration to the respective assigned test sites after completion of baseline assessments. Sunscreen Gel SPF 50 was reapplied to the same designated site after completion of the 120-minute assessments to evaluate the additive moisturization effect of reapplying sunscreen after 2 hours as is directed on sunscreen product labeling. One site was left untreated to serve as a control and the remaining site was unused and not evaluated. Assignment of test materials, untreated control, and unused test sites was in accordance with a predetermined randomization.

Clinical evaluations were conducted over the course of a single visit at baseline and at 15, 60, 90, 120, 180, 240, and 480 minutes after initial application. Subjects participated in the following procedures at the specified time points Clinical Assessment for Dryness and Tactile Roughness Each site was clinically graded for dryness and tactile roughness by a trained clinician at baseline and at 15, 60, 90, 120, 180, and 480 minutes after initial application.

Corneometer Measurements

Triplicate Corneometer CM 825 (Courage+Khazaka, Germany) measurements were taken on each test site to measure test material hydration effects on skin surface at baseline and at 15, 60, 90, 120, 180, and 480 minutes after initial application.

Tewameter Measurements

A single Tewameter® TM300 (Courage+Khazaka, Germany) measurement was taken at each test site to measure the passive transfer of water through the stratum corneum (transepidermal water loss [TEWL]) at baseline and at 15, 60, 90, 120, 180, and 480 minutes after initial application.

Cutometer Measurements

A single Cutometer MPA 580 (Courage+Khazaka, Germany) measurement was taken at each test site to assess the viscoelastic properties of the skin at baseline and at 120, 240, and 480 minutes after initial application.

Overall Conclusions

Overall results of this double-blind, single-center, controlled study indicate that 1 application of Sunscreen Gel SPF 50 and 2 applications (at 2 hours apart) were effective in providing moisture to the skin and improving visual signs of dryness and tactile roughness when compared to the untreated control site over the course of 8 hours on women with mild to moderate dry skin and roughness on the lateral lower legs under these study conditions. A single application was also effective in improving the skin elasticity at the 120-minute time point when compared to the untreated test site. Applications of both test materials did not negatively affect the barrier properties of the skin when compared with an untreated test site. No adverse events were reported.

Procedures and Methods

Prior to the start of the study, potential subjects were screened over the telephone for eligibility criteria through the use of an IRB-approved telephone script. Women between the ages of 18 and 65 years were scheduled for eligibility screening at the clinic. The prospective subjects were advised to avoid application of any moisturizing topical products and to not shave or use any depilatory products on the lower legs for at least 2 days prior to the clinic visit. Prospective subjects were instructed to refrain from drinking hot beverages, ingesting caffeine containing products, eating spicy food, and/or smoking for 1 hour prior to the scheduled visit and for the duration of the study.

At visit 1 (baseline), prospective subjects assigned a screening number and evaluated for the following eligibility criteria:

Presence of Dry Skin and Roughness

Clinically determined mild to moderate dry skin and tactile roughness (score of 1.0 to 3.0 where 0=none and 4=severe) on the lateral lower legs.

Subjects who met all qualification criteria were enrolled into the study and assigned a subject number. A template was used to mark 2 test sites on the lateral side of each subject's lower legs (total of 4 sites per subject). Each test site was approximately 25 cm² in area, with at least 1 cm between each site. Of the 4 sites, 3 were designated for clinical evaluations and 1 was unused/not evaluated in accordance with a predetermined randomization.

Subjects acclimated to ambient temperature and humidity conditions for at least 20 minutes prior to participating in bioinstrumentation procedures.

Upon acclimation, subjects participated in the following baseline procedures:

Clinical Assessment for Dryness

Each test site was clinically graded for dryness using the following numerical definitions (with half-point scores assigned as necessary to accurately describe the skin condition):

0=None
1=Fine, powdery appearance
2=Obvious powdery appearance
3=Small scales (<1.0 mm) still firmly attached, edges curling and uplifting
4=Obvious large scales (>1.0 mm) curled, uplifted and loosely attached Clinical Assessment for Tactile Roughness Each test site was clinically graded for tactile roughness using the following numerical definitions (with half-point scores assigned as necessary to accurately describe the skin condition):

0=Skin feels very smooth, no palpable skin roughness or bumps
1=Mildly palpable skin roughness
2=Obviously palpable skin roughness
3=Moderately palpable skin roughness with drags and/or bumps
4=Significantly (severe) palpable skin roughness with drags and/or bumps Corneometer Measurements Triplicate Corneometer CM 825 (Courage+Khazaka, Germany) measurements were taken on each test site. The Corneometer measures moisture content in the stratum corneum by an electrical capacitance method. The measurement has no units, but is proportional to the dielectric constant of the surface layers of the skin, and increases as the skin becomes more hydrated. The readings are directly related to the skin's electrical capacitance (picoFarads).

Tewameter Measurements

A single Tewameter® TM300 (Courage+Khazaka, Germany) measurement was taken on each test site. The Tewameter measures the passive transfer of water through the stratum corneum (TEWL). The measurement of this water evaporation is based on the diffusion principle in an open chamber and the density gradient is measured indirectly by two pairs of sensors located inside the hollow cylinder probe. Data are analyzed by a microprocessor and reported in g/m2/h.

Cutometer Measurements

A single Cutometer MPA 580 (Courage+Khazaka, Germany) measurement was taken on each test site. The Cutometer was used to assess the viscoelastic properties (i.e. extensibility [R0], resiliency [R2], pure elasticity [R5], and biological elasticity [R7]) of the skin). The instrument applies a vacuum to a small area of skin and measures the elastic response of the skin (movement of the skin into and out of the aperture) by an optical technique. Three hundred mbar of negative pressure was applied and released through an 8-mm probe for 5 seconds of suction, 10 seconds of relaxation time, followed by another 5 seconds of suction and 10 seconds relaxation cycle and measurement was taken.

A clinician applied 100 µL of each of the test materials (Sunscreen Gel SPF 50] to the designated sites (1 test material per site) and the remaining site was left untreated to serve as a control in accordance with a predetermined randomization. Each test material was dispensed using a calibrated pipettor and the test material was gently rubbed into the skin by a clinician using a finger cot.

Approximately 15 (±5), 60 (±10), 90 (±10), and 120 (±15) minutes after the initial test material application, subjects participated in the following procedures as described previously (unless indicated otherwise):

Clinic personnel recorded concomitant medications and questioned subjects regarding changes in their health. AEs were recorded if applicable.

Clinical grading of dryness was performed.
Clinical grading of tactile roughness was performed.
Corneometer and Tewameter measurements were performed.
Cutometer measurements were performed at the 120-minute time point only.

Immediately after completion of the procedures at the 120-minute time point, a clinician reapplied 100 µL of Sunscreen Gel SPF 50 to one of the same assigned test sites which received the initial application.

Approximately 180 (±20), 240 (±20), and 480 (±40) minutes after the initial test material application, subjects participated in the following procedures as described previously at the specified time points:

Clinic personnel recorded concomitant medications and questioned subjects regarding changes in their health. Adverse events (AEs) were recorded if applicable.

At 180-minute and 480-minute time points:
Clinical grading of dryness was performed.
Clinical grading of tactile roughness was performed.
Corneometer and Tewameter measurements were performed.
Cutometer measurements were performed at the 240-minute and 480-minute time points.

Biostatistics and Data Management

The PP population was the primary population for all statistical analyses testing. The PP population included all subjects who were deemed eligible for study participation and completed the study according to protocol. Only the data of completing subjects were analyzed. Subjects may have been removed from the analysis in the case of an AE, an SAE, non-compliance, or Investigator discretion.

The triplicate Corneometer measurements for each subject, location, and time point were averaged prior to statistical analysis.

For the clinical assessment of dryness and tactile roughness and bioinstrumentation measurements (Corneometer, Tewameter, and Cutometer), a descriptive statistical summary is provided, including the number of observations (N), mean, median, standard deviation (SD), minimum (MIN) and maximum (MAX) at all visits. Mean of the change from baseline (defined as the post-baseline value minus the baseline value) was estimated at each applicable post-baseline time point.

Percent mean change from baseline and percentage of subjects showing improvement or worsening were calculated using the following formulas:

Percent mean change from baseline=(visit mean score−baseline mean score)×100 baseline mean score Percent of subjects improved/worsened=(number of subjects improved/worsened from baseline)×100 total number of subjects A comparison between each of the treated test sites to the untreated test site (control) was performed for each parameter. The null hypothesis, that the mean change from baseline is equal between the treated and untreated sites was tested at each applicable post-baseline time point using a Wilcoxon signed-rank test for clinical assessment of dryness and tactile roughness and a mixed model for bioinstrumentation measurements. The mixed model included the change from baseline as response variable, the treatment as a fixed effect, subject as a random effect, and baseline as a covariate. No comparisons were made between the treated test sites.

All statistical tests were 2-sided at significance level alpha=0.05. P-values are reported to 3 decimal places (0.000). No multiple testing corrections were considered in the study. Statistical analyses were performed using SAS software version 9.40 series (SAS Statistical Institute).

Clinical grading and bioinstrumentation measurements were recorded using Stephens electronic data capture (EDC) system. The Stephens EDC is a computerized system designed for the collection of clinical data in electronic format. The 3 major aspects of EDC consist of a graphical user interface for data entry, a validation component to check for user data, and a reporting tool for analysis of the collected data.

The Stephens EDC is compliant with the Food and Drug Administration (FDA) regulations, namely the FDA's 21 CFR Part 11 regulation "Electronic Records; Electronic Signatures", which regulates the use of EDC in trials. Content validation procedures were performed to ensure adequate coverage of critical EDC system features.

Data review and analyses was performed by an independent data committee. The data committee consists of selected representatives from clinical services, quality assurance and the statistical department of Stephens & Associates. When requested, it was the responsibility of the independent data committee to send any interim data reports to the Sponsor.

Detailed Results

Clinical Assessment of Dryness and Tactile Roughness

Comparisons between each of the treated sites to the untreated site, based on the mean change from baseline for clinical assessment, showed a statistically significant difference in favor of each of the treated sites for dryness and tactile roughness at 15, 60, 90, 120, 180, and 480 minutes after initial application.

Corneometer Measurements

Comparisons between each of the treated sites to the untreated site, based on the mean change from baseline for Corneometer measurements, showed a statistically significant difference in the moisture content of the stratum corneum in favor of each of the treated sites at 15, 60, 90, 120, 180, and 480 minutes after initial application.

Tewameter Measurements

Comparisons between each of the treated sites to the untreated site, based on the mean change from baseline for Tewameter measurements, showed no statistically significant differences in the barrier properties of the skin at 15, 60, 90, 120, 180, and 480 minutes after the initial application. The estimated difference between the treated and untreated sites were considerably small [−0.37 to 0.16 for Sunscreen Gel SPF 50 (230, Formula #Y73-161) and −0.18 to 0.01 for Sunscreen Gel SPF 50 (725, Formula #Y73-161)] which concluded that use of the sunscreen did not adversely affect the skin's protective barrier.

Cutometer Measurements

Comparisons between each of the treated sites to the untreated site, based on mean change from baseline for Cutometer measurements, showed a statistically significant difference in favor of site treated with Sunscreen Gel SPF 50 for pure elasticity (R5) at 120 minutes after the initial application. There were no statistically significant differences between the treated sites and untreated site for extensibility (R0), resiliency (R2), or biological elasticity (R7) at any applicable post-application time point.

Overall results of this double-blind, single-center, controlled study indicate that 1 application of Sunscreen Gel SPF 50 and 2 applications (at 2 hours apart) were effective in providing moisture to the skin and improving visual signs of dryness and tactile roughness when compared to the untreated control site over the course of 8 hours on women with mildly to moderately dry skin and roughness on the lateral lower legs under these study conditions. A single application of Sunscreen Gel SPF 50 was also effective in improving the skin elasticity at the 120-minute time point when compared to the untreated test site. Applications of both test materials did not affect the barrier properties of the skin when compared with an untreated test site.

In addition to the cosmetic attributes evaluated and discussed above, the sunscreen Gel was evaluated in a robust battery of standard and proprietary safety tests. Standard safety testing protocols conducted by external investigators to ensure that the product would be non-irritating, and non-sensitizing to skin with and without UV exposure included, Phototoxicity, Photoallergy and Human Repeat Insult Patch Test (HRIPT). A proprietary outdoor use test was also conducted to demonstrate the safety of the product under real use conditions including sun, exercise and swimming pool exposure.

Example 5. Consumer Testing

An assessment of the effects of a disclosed formulation (shown in Table 13) was determined by questioning treated subject regarding the product following use. This study was a monadic in-use evaluation of the product applied to the face. 49 subjects completed the study, after 4 weeks twice daily use of the test product. Questionnaire administration using SurveyTracker Plus® or similar allowed for an efficient and accurate method of determining subject response proportions to assess the consensus opinion of a clinical study population.

Subjects completed a self-assessment questionnaire at Week 4. Responses to questionnaires was tabulated and reported in percentages for each response. Further, responses were coded numerically so that the descriptive analysis for the scores were conducted for each question. Questionnaire responses were analyzed by one sample z-test for proportions. The proportion of subjects choosing the neutral response was split equally and added to the response proportion of the top (positive) and bottom (negative) choices. The Z-test was used to determine whether the proportion of subjects responding positively (including half of the neutral responses) to each question was significantly different from 50%. Statistical significance exists for Z-scores greater than or equal to the absolute value of 1.96 at the 95% confidence level. A summary of consumer responses is shown in Table 14.

TABLE 13

Exemplary Gel Formulation of the Disclosure

| | |
|---|---|
| SD Alcohol 40-B | 50.20% |
| PVP | 3.50% |
| Homosalate | 10.00% |
| Ethylhexyl Salicylate | 4.50% |
| Butyl Methoxydibenzoylmethane | 3.00% |
| Benzophenone-3 | 5.00% |
| Octocrylene | 9.00% |
| Polyester-27 | 1.00% |
| Silica Dimethicone Silylate | 0.70% |
| Acrylates/C12-22 Alkylmethacrylate Copolymer | 1.00% |
| Dimethicone/Vinyl Dimethicone Crosspolymer and Silica | 1.50% |
| Ethylhexyl Isononanoate | 5.00% |
| Beeswax | 0.50% |
| Dicaprylyl Ether | 5.00% |
| Fragrance | 0.10% |
| | 100.00% |

TABLE 14

Questionnaire

| Question | Most Favorable Percentage* | Least Favorable Percentage* | Z-Score | Significant |
|---|---|---|---|---|
| It felt cooling on my skin as I applied it | 93.9% | 6.1% | 6.14 | Yes |
| It left my skin feeling cool | 90.8% | 9.2% | 5.71 | Yes |
| It left my skin feeling hydrated | 83.7% | 16.3% | 4.71 | Yes |
| It left my skin feeling clean from residue | 82.7% | 17.3% | 4.57 | Yes |

Example 6

Exemplary Zinc Oxide Based Gel Formulation of the Disclosure

TABLE 15

An Exemplary Zinc Oxide Based Gel Formulation of This Disclosure

| Ingredient | percentage |
|---|---|
| Ethanol (SD Alcohol 40-B) | 61.70 |
| Polyester-27 | 1.00 |
| Dermol 89 | 5.00 |
| Beeswax | 0.50 |
| Dicaprylyl Ether | 5.00 |
| Silica Dimethicone Silylate | 0.70 |
| Acrylates/C12-22 Alkylmethacrylate Copolymer C5G | 1.00 |
| Dimethicone/Vinyl Dimethicone Crosspolymer | 1.50 |
| Fragrance | 0.10 |

TABLE 15-continued

An Exemplary Zinc Oxide Based Gel Formulation of This Disclosure

| Ingredient | percentage |
|---|---|
| PVP | 3.50 |
| Zinc Nano 20 | 20.00 |
| | 100.00 |

OTHER EMBODIMENTS

The foregoing description discloses only exemplary embodiments of the invention.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

What is claimed is:

1. An anhydrous gel formulation comprising:
   one or more active agents, one or more skin conditioning agents, one or more emollients, one or more film forming agents, one or more viscosity increasing agents, about 40% to about 62% alcohol, the alcohol comprising ethanol;
   the film forming agents comprising about 0.1% to about 1% octyldodecyl/glyceryl hydroxy stearate dilinoleate dimethicone copolymer, about 0.5% to about 2% acrylates/$C_{12-22}$ alkylmethacrylate copolymer, about 1% to about 5% polyvinylpyrrolidone, and about 0.25% to about 1% Beeswax;
   the one or more emollients comprising about 2% to about 10% ethylhexyl isononanoate; and/or about 2% to about 10% dicaprylyl ether;
   the one or more viscosity increasing agents comprising a fumed silica, wherein the fumed silica comprises about 0.25% to about 1% surface-treated with silica dimethicone silylate; and
   the one or more skin conditioning agents comprising about 0.5% to about 2% dimethicone/vinyl dimethicone crosspolymer.

2. The anhydrous gel formulation of claim 1, wherein the anhydrous gel formulation is an anhydrous sunscreen gel formulation and comprises sunscreen active agents.

3. The anhydrous gel formulation of claim 1, further comprising a fragrance.

4. The anhydrous gel formulation of claim 1, further comprising Zinc Oxide.

5. The anhydrous gel formulation of claim 1, further comprising one or more cooling agents.

6. The anhydrous gel formulation of claim 5, the one or more cooling agents comprising an ester of L-menthol and L-pyrrolidone carboxylic acid, linked by a weak bond.

7. The anhydrous gel formulation of claim 6, wherein the one or more cooling agents comprise menthyl ethylamido oxalate.

* * * * *